(12) United States Patent
Vila Ramirez et al.

(10) Patent No.: US 11,504,456 B2
(45) Date of Patent: Nov. 22, 2022

(54) PERCUTANEOUS DRAINAGE DEVICE

(71) Applicant: Inova Medical Pty Ltd, Subiaco (AU)

(72) Inventors: Narciso Vila Ramirez, Singleton (AU); Ming Khoon Yew, Dalkeith (AU); Melanie White, Subiaco (AU); Natasha Ahuja, Southbank (AU); Alex Hayes, Carine (AU)

(73) Assignee: INOVA MEDICAL PTY LTD, Subiaco (AU)

( * ) Notice: Subject to any disclaimer, the term of this patent is extended or adjusted under 35 U.S.C. 154(b) by 396 days.

(21) Appl. No.: 16/464,357

(22) PCT Filed: Nov. 28, 2017

(86) PCT No.: PCT/AU2017/051312
§ 371 (c)(1),
(2) Date: May 28, 2019

(87) PCT Pub. No.: WO2018/094478
PCT Pub. Date: May 31, 2018

(65) Prior Publication Data
US 2021/0113746 A1    Apr. 22, 2021

(30) Foreign Application Priority Data

Nov. 28, 2016 (AU) .............................. 2016904884

(51) Int. Cl.
*A61M 1/00* (2006.01)
*A61B 17/3209* (2006.01)
(Continued)

(52) U.S. Cl.
CPC ..... *A61M 1/0003* (2013.01); *A61B 17/32093* (2013.01); *A61B 17/3423* (2013.01); *A61M 27/00* (2013.01); *A61B 2090/3966* (2016.02)

(58) Field of Classification Search
CPC ...... A61F 9/00772; A61F 2/0811; A61F 2/44; A61F 2/4601; A61F 2250/0071;
(Continued)

(56) References Cited

U.S. PATENT DOCUMENTS 4,772,261 A * 9/1988 Von Hoff ............... A61B 17/68
604/175
5,009,643 A * 4/1991 Reich .................. A61B 17/3421
604/165.02

(Continued)

FOREIGN PATENT DOCUMENTS

AU     2016203963 A1    1/2017
CN     2404489 Y        11/2000
(Continued)

OTHER PUBLICATIONS

ISR/WO associated with PCT/AU2017/051312 and dated Jan. 11, 2018.
(Continued)

*Primary Examiner* — Adam Marcetich
(74) *Attorney, Agent, or Firm* — Vorys, Sater, Seymour and Pease LLP

(57) ABSTRACT

A percutaneous drainage device for draining a fluid collection located under the skin of a patient is disclosed. The percutaneous drainage device includes a penetration component slidably engaged with a cannula. The penetration component has a piercing end adapted to penetrate tissue of a patient and introduce an open end of the cannula to a subcutaneous fluid collection site. The cannula may be held in place in the patient by an anchoring means. The cannula provides a passage through which a fluid collection may be drained from a patient. The cannula may be in fluid com-
(Continued)

munication with a collection vessel, which collects fluid collection transported away from the subcutaneous fluid collection site.

20 Claims, 6 Drawing Sheets

(51) Int. Cl.
*A61B 17/34* (2006.01)
*A61M 27/00* (2006.01)
*A61B 90/00* (2016.01)

(58) Field of Classification Search
CPC ............ A61B 17/3415; A61B 17/3472; A61B 17/864; A61B 2017/349; A61B 17/1671; A61B 17/34; A61B 17/1655; A61M 27/00; A61M 1/0003
See application file for complete search history.

(56) References Cited

U.S. PATENT DOCUMENTS

| | | | |
|---|---|---|---|
| 5,279,567 A | 1/1994 | Ciaglia | |
| 5,372,583 A * | 12/1994 | Roberts | A61M 25/06 600/567 |
| 5,470,308 A | 11/1995 | Edwards et al. | |
| 5,645,547 A * | 7/1997 | Coleman | A61B 17/1615 606/104 |
| 5,735,867 A | 4/1998 | Golser et al. | |
| 6,228,088 B1 * | 5/2001 | Miller | A61M 39/0208 606/80 |
| 6,575,919 B1 * | 6/2003 | Reiley | A61B 17/8819 600/567 |
| 6,607,535 B1 * | 8/2003 | Chan | A61F 2/4614 606/95 |
| 2003/0078592 A1 * | 4/2003 | Heilman | A61B 17/32053 606/108 |
| 2005/0149093 A1 * | 7/2005 | Pokorney | A61B 17/3415 606/185 |
| 2006/0004368 A1 * | 1/2006 | Zaleski | A61B 8/4227 606/75 |
| 2006/0195069 A1 | 8/2006 | Opie et al. | |
| 2006/0276738 A1 * | 12/2006 | Becker | A61F 9/00772 604/8 |
| 2007/0270766 A1 * | 11/2007 | Kucklick | A61M 27/00 604/256 |
| 2008/0004640 A1 * | 1/2008 | Ellingwood | A61B 17/0057 606/151 |
| 2008/0076959 A1 * | 3/2008 | Farnan | A61M 60/148 600/16 |
| 2008/0171989 A1 * | 7/2008 | Bell | A61M 25/0662 604/170.01 |
| 2008/0242930 A1 | 10/2008 | Hanypsiak et al. | |
| 2009/0082778 A1 * | 3/2009 | Beane | A61B 17/0293 604/8 |
| 2009/0306586 A1 | 12/2009 | Ross et al. | |
| 2011/0028985 A1 * | 2/2011 | Vassiliades | A61F 2/064 606/108 |
| 2012/0109111 A1 | 5/2012 | Li | |
| 2012/0323259 A1 | 12/2012 | Richardson | |
| 2013/0123662 A1 | 5/2013 | Hipp | |
| 2013/0123797 A1 | 5/2013 | Livneh | |
| 2014/0024945 A1 | 1/2014 | Mung et al. | |
| 2014/0213931 A1 * | 7/2014 | Lee | A61B 10/025 600/567 |
| 2015/0190163 A1 | 7/2015 | Ciulla et al. | |
| 2016/0067395 A1 * | 3/2016 | Jimenez | A61M 60/135 606/151 |
| 2016/0089180 A1 | 3/2016 | Entabi | |
| 2017/0027551 A1 | 2/2017 | O'Callaghan et al. | |
| 2017/0056043 A1 * | 3/2017 | Jenkins | A61B 17/1688 |
| 2017/0086966 A1 * | 3/2017 | Spenciner | A61B 17/8863 |
| 2018/0021486 A1 * | 1/2018 | Atashroo | A61M 1/67 604/540 |
| 2018/0085138 A1 | 3/2018 | Preiss et al. | |
| 2019/0167291 A1 | 6/2019 | Prior et al. | |
| 2020/0281625 A1 | 9/2020 | Worrel | |
| 2020/0345382 A1 | 11/2020 | Cha et al. | |

FOREIGN PATENT DOCUMENTS

| | | |
|---|---|---|
| CN | 102711900 A | 10/2012 |
| CN | 202459767 U | 10/2012 |
| CN | 194958094 A | 10/2015 |
| EP | 0232600 A1 | 8/1987 |
| EP | 2868335 A1 | 5/2015 |
| GB | 2313316 A | 11/1997 |
| WO | 199520914 | 8/1995 |
| WO | 2009017445 A1 | 2/2009 |
| WO | 2010098905 A1 | 9/2010 |
| WO | 2012109621 A1 | 8/2012 |
| WO | 2018094478 A1 | 5/2018 |

OTHER PUBLICATIONS

EP Search report from corresponding European Patent Application EP17873654 Search completed May 29, 2020.
Office Action for corresponding Chinese application No. 201780084077.3, dated Jan. 6, 2022.
International-type Search for Provisional Patent application for corresponding AU Application No. 2021903549 dated Sep. 30, 2022.

* cited by examiner

PERCUTANEOUS DRAINAGE DEVICE

TECHNICAL FIELD

The present disclosure relates to a device for percutaneous drainage. In particular, the disclosure relates to a device for accessing and draining a fluid collection located under the skin of a patient.

BACKGROUND

Each year several million patients present to emergency rooms seeking medical assistance for skin and soft tissue infections. A majority of these infections are subcutaneous abscesses, which are confined accumulations or collections of pus and dead tissue below the skin. Patients presenting with this common skin condition usually experience pain and can also present with fever or chills.

The treatment of abscesses is one of the most commonly performed hospital procedures. Some abscesses are 'simple' or 'pointing' and are almost ready to burst through the skin. These abscesses can typically be treated in an outpatient setting with local anaesthetic via an incision and drainage procedure. After administration of a local anaesthetic, a small incision is made at the site to puncture the skin. Contents of the abscess can then escape by draining out through the incision, sometimes assisted by manual expression of the contents by a clinician. Contents of the abscess may project upward and outward when excised and clinicians typically use personal protective equipment to mitigate risk of self-contamination.

Abscesses which are extensively large, deep, or which have thick or non-homogenous contents can be more challenging to drain. Some can be drained using imaging guidance to place a needle, catheter or other suitable drain through the skin into the abscess to remove or drain the fluid collection. However, the drains most commonly inserted often become occluded with abscess contents and stop flowing before the entire contents have been cleared. The patient then requires surgery to open the abscess using a larger incision.

Presently, the majority of complex abscess cases presenting to hospitals are treated in theatre with surgery and under a general anaesthetic. Whilst surgical treatment generally resolves the problem of the abscess, it generates a series of new problems. Patients undergoing surgical abscess treatment typically require a one to two day hospital stay. They must be fasted prior to surgery and face the risks associated with administration of general anaesthesia. Surgical treatment of abscesses requires an incision that needs to be long and deep enough to allow access to the abscess cavity. Typically, the incision will extend across the entire diameter of the abscess and, consequently, scarring may become of concern to the patient. Further, the use of longitudinal force to penetrate skin and tissue to reach the abscess carries a risk of inadvertently puncturing underlying tissue structures.

Surgical treatment of abscesses is thus financially costly for the health care system and patient and also carries risks associated with surgery and administration of general anaesthesia.

Other medical procedures may similarly require access to a fluid collection site in the body of a patient to drain a fluid, which may be liquid or gas. At least some of these medical procedures share similar problems and risks to abscess drainage procedures.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to a first aspect, there is disclosed a percutaneous drainage device comprising a penetration component slidably engaged with a cannula. The penetration component has a piercing end adapted to penetrate tissue of a patient and introduce an open end of the cannula to a subcutaneous fluid collection site, wherein the cannula provides a passage through which a fluid collection may be drained from the patient.

The penetration component may be slidably located in the cannula and be movable between a first position in which the penetration component is located concentric to the cannula; and a second position in which the penetration component is retracted and separated from the cannula. In one embodiment, the penetration component is located in a lumen of the cannula when in the first position.

The penetration component may have a threaded portion at or adjacent the piercing end. The threaded portion may be tapered towards the piercing end. The threaded portion assists the penetration component to drive or drill into the tissue of the patient in use, towards a subcutaneous fluid collection site. The threaded portion may have one or more thread turns.

The piercing end may optionally be provided with a cutting tool or pointed tip to create an initial incision into patient tissue. The cutting tool or pointed tip may be removed or retracted prior to driving or drilling the penetration component into patient tissue.

The piercing end may be driven into patient tissue by rotation of the penetration component about a longitudinal axis thereof. Rotation may be actuated by rotational manipulation of a handle, located at an end of the penetration component opposite to the piercing end. Rotation of the piercing end into patient tissue enables gradual stretching of tissue and smooth introduction of one end of the cannula into tissue and towards the subcutaneous fluid collection site.

The penetration component may be prevented from rotating inside the lumen of the cannula by a securing means. The cannula may also be rotated with the penetration component by rotational manipulation of the handle, thereby driving both penetration component and cannula into tissue of the patient.

The penetration component may have tight tolerance with the lumen of the cannula to generate a negative pressure during retraction of the penetration component from the cannula. This may assist with initial suction of fluid collection.

At least part of an outer surface of the cannula may be threaded to assist in drilling and thereby driving the percutaneous drainage device into patient tissue and towards the fluid collection site.

At least part of one or both of the penetration component and cannula may be comprised of a radiopaque material. The percutaneous drainage device may be provided with one or more radiopaque depth markings.

A length of the cannula may be adjusted following removal of the penetration component by cutting or snapping a frangible portion. A portion of the cannula may protrude from the skin of the patient following any adjustment of cannula length. The cannula may be removed from the patient following removal of the penetration component or remain in situ for a period of time.

The cannula may be secured in situ in the patient by an anchoring means. The anchoring means may comprise a clamp, such as a hinged clamp, which clamps around an outer circumference of the portion of cannula protruding from the patient. The anchoring means may also have an adhesive portion which may attach directly to skin of the patient immediately surrounding the cannula.

The percutaneous drainage device may be provided with a collection management component or collection vessel. The collection vessel is arranged in use to be in fluid communication with the cannula and receive fluid collection that drains from the patient through the cannula.

The collection vessel may attach to the anchoring means by a connector means, to enable attachment, removal and replacement of the collection vessel as required.

The collection vessel may include a pressure regulation means for generating negative pressure in the collection vessel, which may include a valve means.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the disclosure are now described, by way of example only, with reference to the accompanying drawings in which.

In the drawings, like reference numerals designate similar parts.

DESCRIPTION OF EMBODIMENTS

Embodiments of a percutaneous drainage device will now be described by way of example only.

Figure 1:
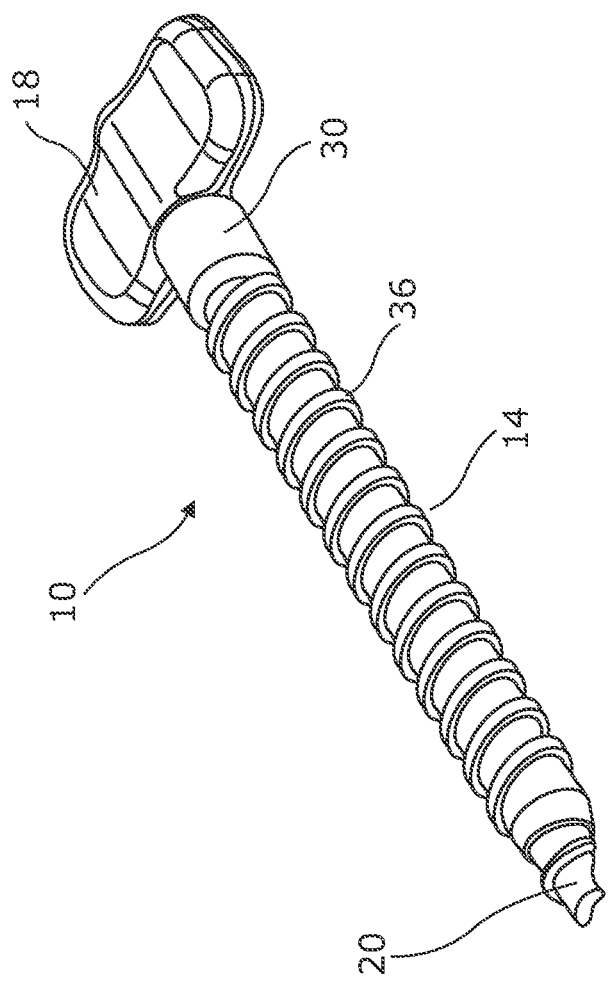
FIG. 1 is a percutaneous drainage device according to one embodiment of the present disclosure.

Referring initially to FIG. 1, there is shown a percutaneous drainage device 10 having application in drainage of a subcutaneous fluid collection from a patient. The percutaneous drainage device 10 is useful for and will be described primarily in the context of draining an abscess. However, it should be understood that the percutaneous drainage device 10 of the present disclosure has utility in gaining access to and drainage of any subcutaneous fluid collection and that the subcutaneous fluid collection may be liquid and/or gas. In the context of drainage of an abscess, 'fluid collection' refers to a collection of pus, liquefied tissue and any other associated liquid held within the confines of an abscess wall.

Figure 2:
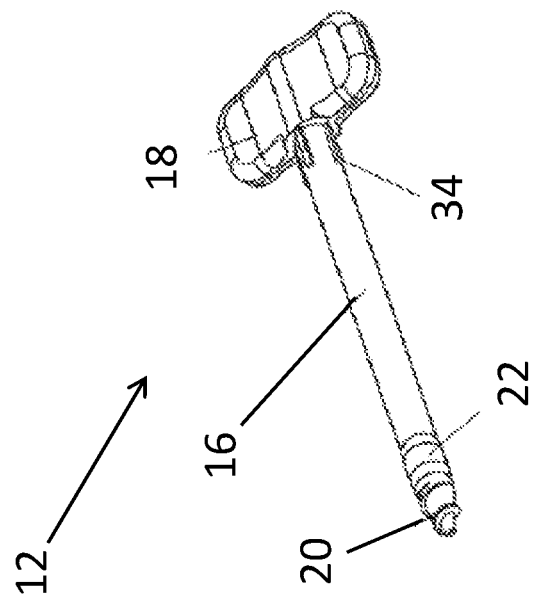
FIG. 2 is one embodiment of a penetration component of the percutaneous drainage device of FIG. 1.
Figure 3:
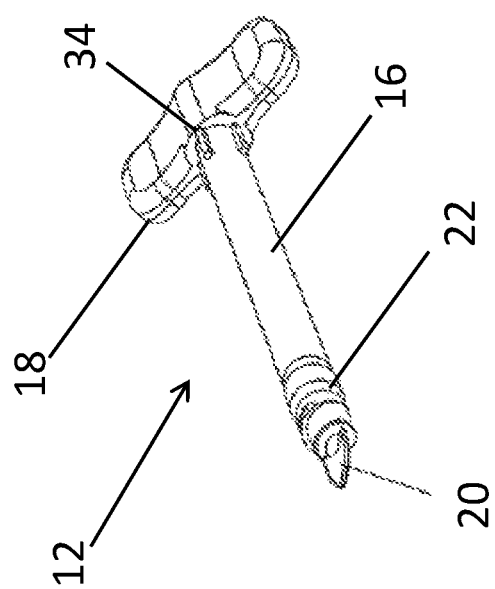
FIG. 3 is a further embodiment of a penetration component of the percutaneous drainage device of FIG. 1.

The percutaneous drainage device 10 comprises a cannula 14 having a lumen 24, a first open end 28 and an opposing second open end 30. The cannula 14 may be slidably engaged with a penetration component 12 comprising an elongate shaft 16 having a handle 18 at one end and an opposing piercing or drilling end 20. The penetration component 12 is movable between a first position in which the cannula 14 is concentric to the elongate shaft 16 of the penetration component 12; and a second position in which the penetration component 12 is retracted from and separated from the cannula 14, as shown in FIGS. 2 and 3. In the first position, the penetration component 12 may be located substantially inside the lumen 24 of the cannula 14, as shown in FIG. 1.

In the embodiment shown in the Figures, the penetration component 12 may be prevented from rotating inside the lumen 24 of the cannula 14 when in the first position by a securing means. In the embodiment shown in FIGS. 2 to 4, the securing means comprises one or more grooves 32 disposed on a surface of the lumen 24 adjacent the second open end 30 of the cannula 14. The one or more grooves 32 engage with one or more corresponding ribs 34 disposed on an end of the penetration component 12 adjacent the handle 18.

A first embodiment of the penetration component 12 is shown in FIG. 2. In this embodiment, the penetration component 12 comprises an elongate shaft 16 with a handle 18 at one end and an opposing drilling or piercing end 20. In the embodiment shown in FIG. 2, the piercing end 20 is a cutting tool, such as a small blade.

A second embodiment of the penetration component 12 is shown in FIG. 3, where the piercing end 20 comprises a pointed tip. The piercing end 20 can be used to pierce or perform an initial incision into skin and tissue of the patient, creating an initial aperture. The cutting tool or pointed tip may be retracted or otherwise removed prior to driving or otherwise further introducing the percutaneous drainage device 10 into the tissue of the patient and towards a subcutaneous fluid collection site.

The elongate shaft 16 of the penetration component 12 has a threaded portion 22 at or adjacent the piercing end 20. In the embodiments shown, the threaded portion 22 is tapered towards the piercing end 20, providing a tapered tip with a helical ridge on a surface thereof. At least part of the threaded portion 22 extends outwardly from the first open end 28 of the cannula 14 when the penetration component 12 is in the first position. The threaded portion 22 may have one or more thread turns.

The threaded portion 22 provides the ability to drill and drive into the body of the patient when the penetration component 12 is rotated about the longitudinal axis. This rotation and initial driving of the threaded portion 22 of the penetration component 12 steadily and gradually stretches and increases the aperture of the initial incision. As the penetration component 12 is drilled and driven into the body of the patient, the aperture of the initial incision can be increased to a size that enables smooth introduction of the cannula 14.

The threaded portion 22 can be drilled and driven into tissue by rotation of the elongate shaft 16. Rotation is actuated by rotational manipulation of the handle 18. This mechanism advantageously requires low or minimal longitudinal force to create a passage through the tissue overlying the abscess. Application of minimal longitudinal force can mitigate risk of accidental puncture or damage to the patient.

The penetration component 12 may have a tight tolerance with the lumen 24 of the cannula 14 so as to in use, generate a negative pressure during retraction of the penetration component 12 from the cannula 14. A portion of the elongate shaft 16 of the penetration component 12 may have a bulge portion (not shown), having an outer diameter which is larger relative to the remainder of the elongate shaft 16, to further reduce tolerance with the cannula 14 and form a seal therein. The bulge portion can be located adjacent the threaded portion 22. The bulge portion may, in use, further assist in generation of a negative pressure when retracting the penetration component 12 from the cannula 14. This may assist with initial suction of fluid collection once the percutaneous drainage device 10 has been appropriately positioned in the patient tissue and fluid collection site.

Figure 4:
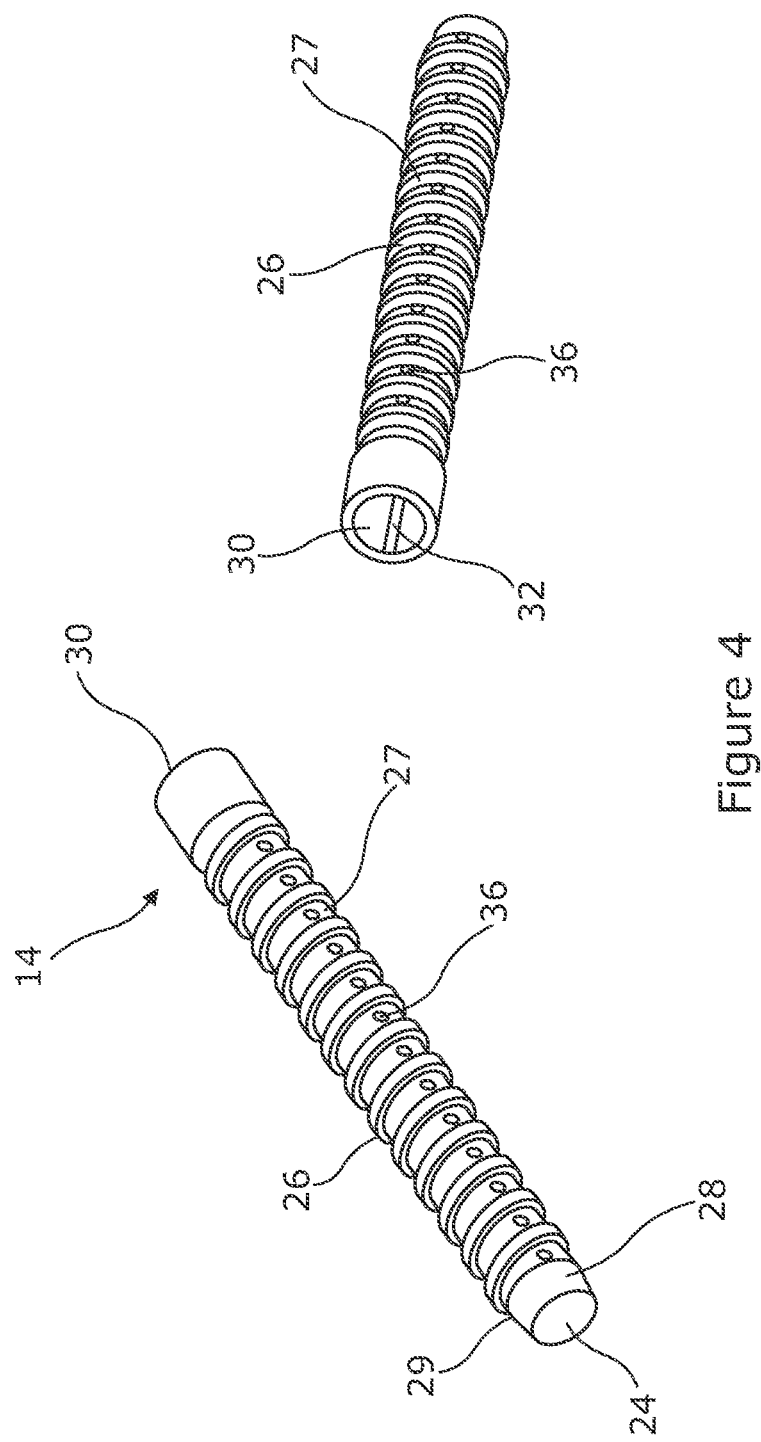
FIG. 4 is a front and rear perspective view of a cannula of the percutaneous drainage device of FIG. 1.

The cannula 14, an embodiment of which is shown in FIG. 4, comprises an elongate hollow cylinder 26 which may be flexible or rigid. The cannula 14 may be made from a bio-stable or bio-resorbable material which can be cut by a standard surgical cutting implement such as scissors. Alternatively, the cannula 14 may be made from a material which can be snapped or broken. The cannula 14 may be snapped or broken along one or more frangible portions disposed at intervals along the length of the elongate hollow cylinder 26. The length of the cannula 14 may therefore be adjusted as required by cutting or snapping along the length of the elongate hollow cylinder 26.

The lumen 24 of the cannula 14 may have a diameter comparable to a diameter of the elongate shaft 16 of the penetration component 12. The diameter of the lumen 24 may be sufficiently large to enable flow and drainage of fluid collection from the body of a patient with minimal risk of blockage.

The cannula 14 may be concentric to the elongate shaft 16 of the penetration component 12. When in the first position, the elongate shaft 16 may sit inside the lumen 24 and at least part of the piercing tip 20 of the penetration component 12 may extend outwardly from the first open end 28, as shown in FIG. 1. The first open end 28 may have a bevel or chamfer to provide a smooth transition with the penetration component 12 when in the first position and when the percutaneous drainage device 10 is driven or otherwise introduced into patient tissue.

At least part of an outer surface of the cannula 14 may be threaded, providing a threaded surface 27. In the embodiment shown in the Figures, a majority of the outer surface is threaded. The threaded surface 27 can assist drilling and driving of the percutaneous drainage device 10 into patient tissue. The cannula 14 with penetration component 12 located and fastened therein by securing means can be driven into tissue by rotational manipulation of the handle 18.

The cannula 14 may be provided with one or more castellations or orifices 29 adjacent the first open end 28 to prevent vacuum sealing when the cannula 14 is in contact with tissue. The cannula 14 may also be provided with markings 36 on the outer surface to provide guidance on depth location of the abscess. The markings 36 can be etched, printed, indented or otherwise provided on the surface of the cannula 14.

At least part of one or both of the penetration component 12 and cannula 14 may be comprised of a radiopaque material. One or more radiopaque depth markings (not shown) may be present on the surface of the cannula 14. The percutaneous drainage device 10 may therefore be introduced and guided into the patient and towards and into the subcutaneous fluid collection site with imaging guidance such as ultrasound.

Figure 5:
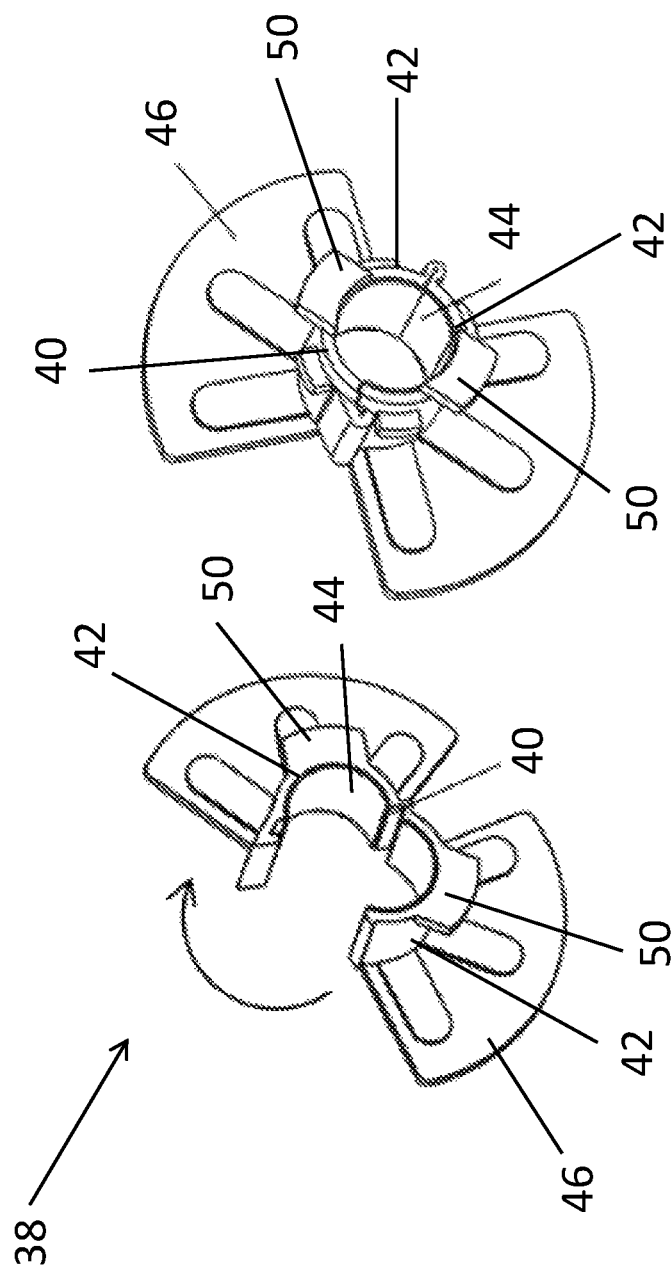
FIG. 5a is an embodiment of an anchoring means of the percutaneous drainage device in an open position.
FIG. 5b is the anchoring means in a closed position.

The percutaneous drainage device 10 may be further provided with an anchoring means 38 or anchoring subassembly. In the embodiment shown in FIGS. 5a and 5b, the anchoring means 38 comprises a hinged clamp 40 comprising a pair of semi-cylindrical or semi-circular portions or halves 42, hingedly connected to each other. The semi-cylindrical portions 42 are movable between an open position, shown in FIG. 5a, and a closed or locked position, shown in FIG. 5b.

The semi-cylindrical portions 42 can be locked in the closed position by a securing means, such as a simple latch mechanism. Once locked, the semi-cylindrical portions 42 form a cylinder or circle having an interface or inner surface 44 with a circumference comparable to an outer circumference of the cannula 14. The semi-cylindrical portions 42 can be made from a rigid material whereby when the hinged clamp 40 is in a closed position, the inner surface 44 provides a rigid interface.

The anchoring means 38 further includes an adhesive portion 46, extending radially outwardly from the semi-cylindrical portions 42. In the embodiment shown, the adhesive portion 46 comprises an adhesive pad, disposed perpendicularly to the axes of the semi-cylindrical portions 42. The adhesive pad may be flexible and attaches directly to the patients skin.

The hinged clamp 40 with inner surface 44 may clamp around the elongate hollow cylinder 26 of the cannula 14. The hinged clamp 40 may be fastened in place around the cannula 14 by suitable means such as friction fit or adhesive. Alternatively, the inner surface 44 may be threaded or have other suitable configuration so that it can be mechanically attached to the cannula 14.

The anchoring means 38 may be further provided with a connector means to enable the anchoring means 38 to connect to a collection management component or collection vessel 48. In the embodiment shown in FIGS. 5a, 5b and 6, the connector means comprises a pair of flanges 50, extending radially outwards from an end of the cylinder or circle formed when the semi-cylindrical portions 42 are in the closed position. The flanges 50 are adapted to slot into a corresponding aperture 52 in a wall of the collection vessel 48. Once the flanges 50 are inserted through the aperture 52 and into an interior of the collection vessel 48, the collection vessel 48 can be rotated, securing the collection vessel 48 onto the anchoring means 38 by a twist lock mechanism. The collection vessel 48 can be removed by counter-rotation and pulling the flanges 50 out of the aperture 52. The collection vessel 48 may therefore be changed or replaced as required.

Figure 6:
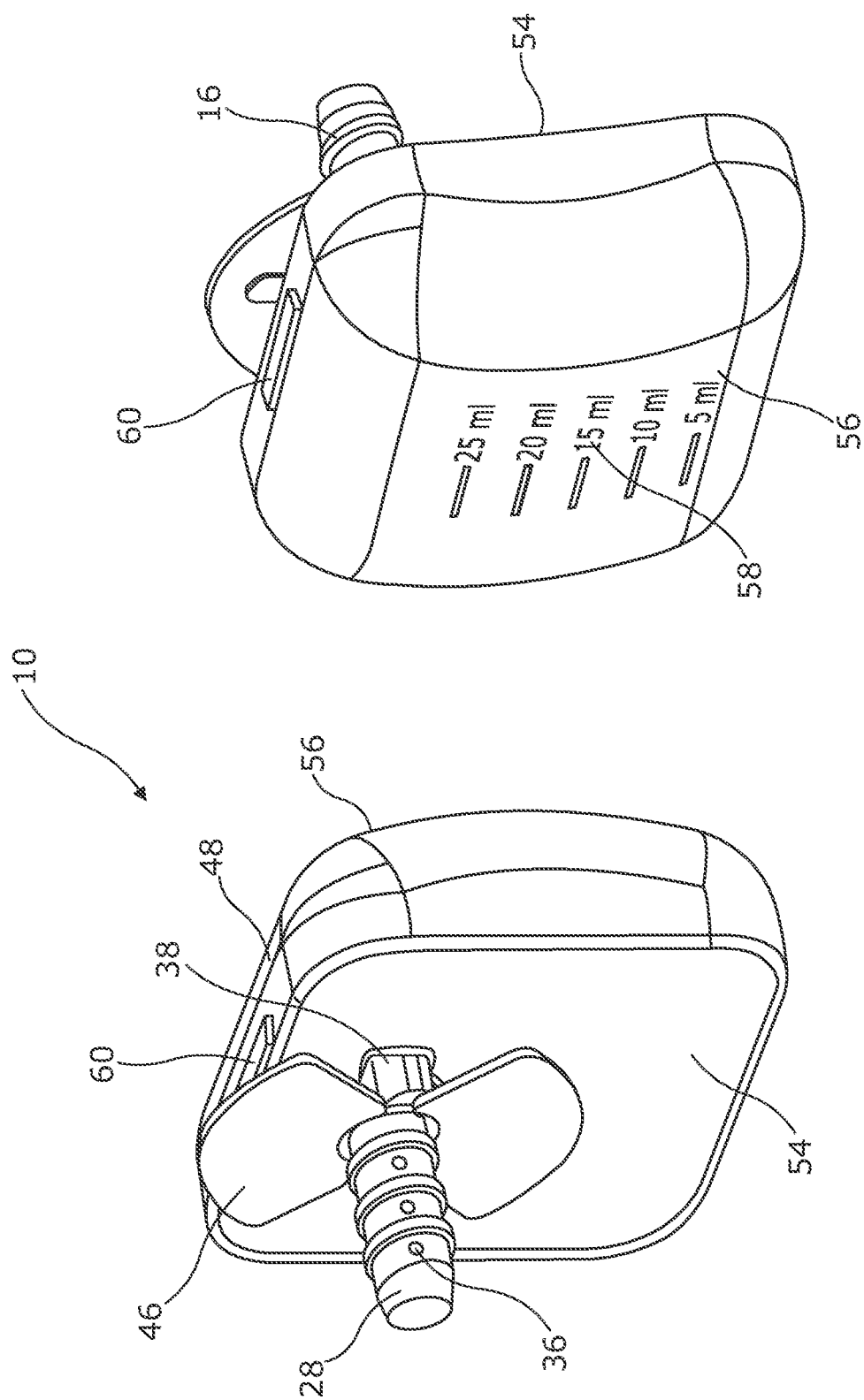
FIG. 6 is a rear and front perspective of a fluid collection vessel of the percutaneous drainage device.

One embodiment of the collection vessel 48 is shown in FIG. 6. In this embodiment, the collection vessel 48 comprises a hollow container or reservoir having a rear wall 54 through which the aperture 52 is located. A front wall 56 of the collection vessel 48 may have markings 58 on an outer surface thereof, which can be printed, etched or labelled to provide guidance on the quantity of collection discharged from the abscess. The collection vessel 48 has a slim or flattened configuration to minimise the amount of protrusion from the body of the patient. In one embodiment, the collection vessel 48 has size and configuration so as to protrude no more than about 40 mm, ideally no more than 35 mm, from the patient's body.

The collection vessel 48 may be a rigid, semi-rigid or absorbent reservoir. If rigid or semi-rigid, the collection vessel 48 may have means for providing negative pressure, to assist in suction of fluid collection from the patient once the percutaneous drainage device 10 has been appropriately positioned in the patient. The collection vessel 48 may be provided with one or more apertures 58 to equalise atmospheric pressure in the collection vessel 48.

The collection vessel 48 may include a pressure regulation means (not shown) for generating negative pressure inside the collection vessel 48. In one embodiment, the pressure regulation means may include a valve 60. The valve 60 may be a one-way valve. The clinician or other operator may compress or inwardly press a deformable part of the collection vessel 48 or a part thereof to expel gas from the collection vessel 48 through the valve 60. As the collection vessel 48 or part thereof begins to return towards an undeformed state, negative pressure is created inside the collection vessel 48, providing suction of collection fluid through the cannula 14 and into the collection vessel 48.

Figure 7:
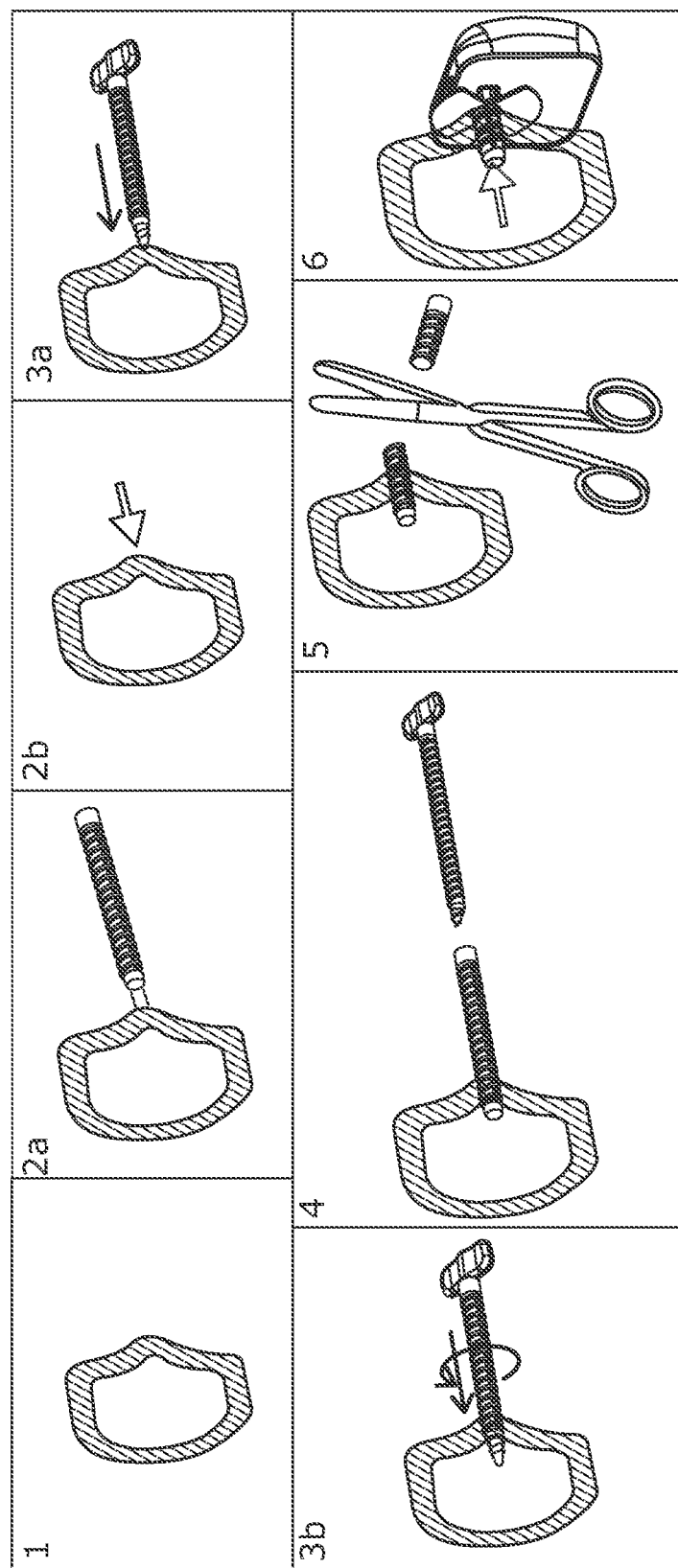
FIG. 7 is a representation of a sequence of steps of use of the percutaneous drainage device of the present disclosure.

Referring to FIG. 7, there is shown a sequence of steps of use of the percutaneous drainage device 10 of the present disclosure, though it should be understood that the sequence of steps may vary depending on clinician preferences. The abscess or other fluid collection present in the patient is first located by the clinician. Following administration of a local anaesthetic around the target site, an initial incision is made into the tissue, either by a conventional scalpel (step 2a) or by the piercing tip 20 of the penetration component 12. Once the initial incision is made, the piercing tip 20 may be retracted or otherwise removed prior to driving the percutaneous drainage device 10 into the tissue of the patient.

The clinician may then commence driving the percutaneous drainage device 10 into the tissue by manual rotation of the handle 18 and penetration component 12 with surrounding cannula 14 (steps 3a and 3b). Driving and positioning of the percutaneous drainage device 10 in the patient may be assisted by imaging guidance, such as ultrasound or fluoroscopy. The threaded portion 22 of the penetration component 12 assists the driving function of the percutaneous drainage device 10, converting torsional energy into linear motion. Advantageously, this can provide greater positional control whilst simultaneously reducing need for downwards force into the tissue. As the penetration component 12 is driven into the tissue, the threaded portion 22 gently stretches cutaneous tissue onto the cannula 14 which may assist in reducing site morbidity. Threading on the surface of the cannula 14 may also assist the percutaneous drainage device 10 to drive further into the tissue and towards the target fluid collection site.

The clinician may determine that the first open end 28 of the cannula 14 has reached the target fluid collection site by imaging guidance. Once the first open end 28 of the cannula 14 has reached the abscess or target fluid collection site, the clinician may grasp the handle 18 of the penetration component 12 and pull away from the body of the patient to retract the penetration component 12, removing it from the cannula 14 (step 4) through the second open end 30. The clinician may further confirm that the first open end 28 of the cannula 14 is appropriately positioned in the target fluid collection site by visually observing presence of pus or other fluid upon retraction of the penetration component 12. The tight tolerance between the penetration component 12 and cannula 14 can generate a negative pressure during retraction of the penetration component 12 from the cannula 14, initiating suction and flow of fluid collection from the abscess and into the lumen 24 of the cannula 14. The cannula 14 thereby provides an extraction pathway through which the abscess contents may drain from the patient's body.

Holding the cannula 14 in place with the bevelled or chamfered first open end 28 positioned in situ in the abscess or target fluid collection, the length of the cannula 14 can be trimmed as required. The cannula 14 may be cut to size using scissors (step 5), or snapped along an appropriate frangible portion. The cannula 14 may be trimmed so that a small portion remains protruding from the skin of the patient. The portion of cannula 14 protruding from the skin of the patient may be sufficiently long to enable attachment of the anchoring means 38.

The cannula 14 is held in place and secured to the patient by the anchoring means 38, which is attached to the portion of cannula 14 protruding from the patients skin. In the embodiment shown in the Figures, the hinged clamp 40 with rigid inner surface 44 is attached to the portion of cannula 14 protruding from the patients skin. The hinged clamp 40 may be positioned on the cannula 14 such that the pair of flanges 50 extend radially from the outermost end of the cannula 14. The adhesive portion 46 of the anchoring means 38 may be attached directly to the patients skin.

The dual attachment of the anchoring means 38 to both the cannula 14 and the patient's skin provides an anchor to maintain the cannula 14 in position and to attach the collection vessel 48 if required. The collection vessel 48 may be attached to the anchoring means 38 by the connector means. In the embodiment shown, the flanges 50 of the anchoring means 38, which extend radially from the outermost end of the protruding cannula 14, are aligned with and pushed through the corresponding aperture 52 in the wall of the collection vessel 48. The collection vessel 48 is then rotated approximately 90° to lock the collection vessel 48 onto the anchoring means 38.

The clinician may activate the pressure regulation means to generate negative pressure inside the collection vessel 48. The clinician can compress the deformable part of the collection vessel 48, reducing the volume inside the collection vessel 48, expelling air through the valve 60 and generating negative pressure. As the collection vessel 48 returns to an undeformed state and pressure begins to equalise inside the collection vessel 48, fluid is suctioned out of the fluid collection site and into the cannula 14.

With the collection vessel 48 so attached and in fluid communication with the cannula 14 via aperture 52, collection fluid may travel from the patient's body through the cannula 14 and into the collection vessel 48 (step 6). The cannula 14 may remain percutaneously in situ for a period of time, typically up to seven days, or until such time as it is deemed that the fluid collection has been appropriately drained. The cannula 14 thus acts to maintain an opening in the skin and subcutaneous fat to permit drainage of the fluid collection over time.

Alternatively, the cannula 14 can be removed shortly after removal of the penetration component 12. Prior to removal, the cannula 14 can provide a passage through which fluid, comprising liquid and/or gas, may exit or drain from the patient. Following removal of the cannula 14, a passage created in the tissue by introduction of the percutaneous drainage device 10 may still permit drainage of fluid from the patient.

Markings 58 on the outer surface of the collection vessel 48 provide an indication of how much fluid has been drained from the patient. The collection vessel 48 can be detached and removed from the anchoring means 38 when desired. The collection vessel 48 may be discarded or sent to a laboratory for analysis of the contents. If further fluid is to be drained, the removed collection vessel 48 can be replaced by a fresh collection vessel 48. The percutaneous drainage device 10 of the present disclosure thus combines percutaneous access and drainage of an abscess as well as ongoing management of the abscess contents during healing.

Once it has been determined that the abscess has been sufficiently drained, the cannula 14 may be removed from the patient. All components of the percutaneous drainage device 10 may be discarded following use.

The percutaneous drainage device 10 of the present disclosure, when placed percutaneously substantially as described above, advantageously provides a low pressure channel and passage for thick, complex collections comprising any combination of pus, debris and dead tissue, to flow out from within the subcutaneous abscess.

The percutaneous drainage device 10 of the present disclosure conveniently provides all the components required to offer a minimally invasive therapy that can be used to treat an abscess. A clinician using the percutaneous drainage device 10 can quickly and easily drain an abscess or other similar subcutaneous fluid collection in a setting which does not require hospital admission. The percutaneous drainage device 10 of the present disclosure therefore advantageously shifts the treatment of abscesses and other subcutaneous fluid collections from a high-cost setting requiring hospital inpatient admission, theatre time and associated patient risk, to a relatively low-cost outpatient procedure with reduced clinical care time and associate patient risk.

EXAMPLE

The following series of tests were performed, using embodiments of the penetration component 12 with specifications as set out in Table 1 below.

| Penetration Component | A | B | C | D |
|---|---|---|---|---|
| Thread Turns | 1.5 | 3 | 2 | 3 |
| Helix taper angle | 12 | 12 | 8 | 8 |
| Thread pitch (mm) | 3 | 2 | 2 | 2 |
| Incision required | Yes | Yes | Yes | Yes |
| Skin damage | Some | Moderate | Yes | Minimal |
| Ease of entry | No | Yes - at 1 cm depth | Yes | Yes |
| Easy to remove | Yes | Yes | Yes | Moderately |

Each penetration component A-D was tested to determine (i) ability to enter and drive into tissue upon application of rotational force; (ii) whether or not an initial incision was required; (iii) level of damage or twisting to skin; and (iv) how easy the penetration component could be removed from the tissue. The results of these tests are also included in Table 1 above. Each penetration component was tested on an upper thigh region of a fresh frozen cadaver.

In each case, an initial incision in the skin was required prior to introducing the piercing point of the penetration component. Test penetration components A and C caused twisting of the skin upon entry, indicating that they could cause damage to the surrounding tissue. Test penetration components B and D showed less damage to the skin, with test penetration component D causing the least damage.

Test penetration components A and B were able to drive into the tissue only after application of axial pressure. Test penetration component A required application of significant axial pressure and reached a depth of 3 cm only. Test penetration component B required initial application of axial pressure but started to drive into the tissue once a depth of about 1 cm was reached. Test penetration component C was able to tunnel into the tissue to a depth of about 1 cm with application of rotational force only. Minimal axial pressure was required to drive further to a measured depth of about 3 cm. Test penetration component D required little or no axial pressure to commence and continue driving into the tissue.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A percutaneous drainage device comprising a penetration component slidably engaged with a cannula, the penetration component having a piercing end arranged to penetrate tissue of a patient and introduce an open end of the cannula to a subcutaneous fluid collection site, wherein the cannula defines a lumen through which a fluid collection may be drained from the patient,
   wherein the penetration component is movable between a first position, in which the penetration component is located concentrically within the lumen, and a second position, in which the penetration component is retracted and separate from the cannula, and
   wherein a portion of the penetration component exhibits an outer diameter larger than remaining portions of the penetration component and thereby generates a tight tolerance between the lumen and the penetration component, which generates a negative pressure in the lumen upon retracting the penetration component from the cannula and thereby causes initial suction of the fluid collection into the cannula.

2. The percutaneous drainage device of claim 1, wherein the penetration component has a threaded portion at or adjacent the piercing end, whereby rotation of the penetration component assists the piercing end to drive into the tissue of the patient toward a subcutaneous fluid collection site.

3. The percutaneous drainage device of claim 2, wherein the threaded portion is tapered towards the piercing end, and/or has one or more thread turns.

4. The percutaneous drainage device of claim 1, wherein the penetration component is prevented from rotating inside the lumen by a securing means.

5. The percutaneous drainage device of claim 4, wherein the securing means comprises one or more grooves disposed on a surface of the lumen, the one or more grooves configured to engage with one or more corresponding ribs on the penetration component.

6. The percutaneous drainage device of claim 1, wherein the piercing end is provided with a cutting tool, wherein the cutting tool is fixed, retractable or removable.

7. The percutaneous drainage device of claim 1, wherein the piercing end and/or cannula is driven into patient tissue by rotation of the penetration component.

8. The percutaneous drainage device of claim 1, wherein the piercing end is driven into patient tissue by rotation of the penetration component and rotation is actuated by rotational manipulation of a handle.

9. The percutaneous drainage device of claim 1, wherein at least part of an outer surface of the cannula is threaded.

10. The percutaneous drainage device of claim 1, wherein a length of the cannula is adjustable.

11. The percutaneous drainage device of claim 1, wherein a length of the cannula is adjustable by cutting or by breaking along a frangible portion.

12. The percutaneous drainage device of claim 1, further comprising an anchoring means that comprises:

a hinged clamp including a pair of semi-cylindrical halves adapted to clamp around an outer circumference of a portion of the cannula protruding from the patient; and an adhesive portion extending radially outwardly from the pair of semi-cylindrical halves and configured to attach to skin of the patient.

13. The percutaneous drainage device of claim 12, wherein the hinged clamp is fastened in place around the outer circumference of the portion of the cannula using at least one of a friction fit, an adhesive, and threading.

14. The percutaneous drainage device of claim 1, further comprising a collection vessel in fluid communication with the cannula.

15. The percutaneous drainage device of claim 1, further comprising a collection vessel in fluid communication with the cannula, wherein the collection vessel is detachable and attaches to an anchoring means by a connector means.

16. The percutaneous drainage device of claim 1, further comprising a collection vessel in fluid communication with the cannula, wherein the collection vessel has a pressure regulation means for generating negative pressure in the collection vessel.

17. The percutaneous drainage device of claim 1, wherein at least part of one or both of the penetration component and the cannula comprise a radiopaque material.

18. The percutaneous drainage device of claim 1, wherein the fluid collection is a liquid and/or gas.

19. The percutaneous drainage device of claim 1, wherein the portion of the penetration component that exhibits the outer diameter larger than remaining portions of the penetration component comprises a bulge portion forming an integral part of the penetration component.

20. The percutaneous drainage device of claim 1, wherein an orifice is defined on a sidewall of the cannula at the open end to prevent vacuum sealing when the cannula is in contact with tissue.

* * * * *